United States Patent
Overcast

(10) Patent No.: US 10,054,576 B2
(45) Date of Patent: Aug. 21, 2018

(54) SYSTEM AND DEVICE FOR NEARFIELD GUNSHOT AND EXPLOSION DETECTION

(71) Applicant: Tracer Technology Systems Inc., Billings, MT (US)

(72) Inventor: Allan Ward Overcast, Billings, MT (US)

(*) Notice: Subject to any disclaimer, the term of this patent is extended or adjusted under 35 U.S.C. 154(b) by 510 days.

(21) Appl. No.: 14/832,975

(22) Filed: Aug. 21, 2015

(65) Prior Publication Data
US 2016/0209390 A1    Jul. 21, 2016

Related U.S. Application Data

(60) Provisional application No. 62/043,515, filed on Aug. 29, 2014.

(51) Int. Cl.
| | | |
|---|---|---|
| G01N 33/22 | (2006.01) | |
| G08B 29/18 | (2006.01) | |
| H04R 29/00 | (2006.01) | |
| G08B 13/16 | (2006.01) | |
| G08B 25/01 | (2006.01) | |

(52) U.S. Cl.
CPC ......... *G01N 33/227* (2013.01); *G08B 29/188* (2013.01); *G08B 13/1672* (2013.01); *G08B 25/016* (2013.01); *H04R 29/004* (2013.01)

(58) Field of Classification Search
CPC .................................................. G01N 33/227
See application file for complete search history.

(56) References Cited

U.S. PATENT DOCUMENTS

| | | | |
|---|---|---|---|
| 5,241,518 A | 8/1993 | McNelis et al. | |
| 5,355,350 A * | 10/1994 | Bass | G01H 3/12 |
| | | | 73/170.16 |
| 5,544,129 A | 8/1996 | McNelis | |
| 5,790,019 A * | 8/1998 | Edwin | G08B 7/06 |
| | | | 340/286.02 |
| 5,930,202 A | 7/1999 | Duckworth et al. | |
| 6,178,141 B1 | 1/2001 | Duckworth et al. | |
| 6,281,792 B1 | 8/2001 | Lerg et al. | |
| 7,126,877 B2 | 10/2006 | Barger et al. | |
| 7,266,045 B2 | 9/2007 | Baxter et al. | |
| 7,408,840 B2 | 8/2008 | Barger et al. | |
| 7,688,679 B2 | 3/2010 | Baxter et al. | |
| 7,750,814 B2 | 7/2010 | Fisher et al. | |
| 8,036,065 B2 | 10/2011 | Baxter et al. | |

(Continued)

*Primary Examiner* — Lisa Caputo
*Assistant Examiner* — Alex Devito
(74) *Attorney, Agent, or Firm* — Antoinette M. Tease

(57) ABSTRACT

A computer-implemented system for nearfield gunshot and explosion detection comprising a hardware device with a differential air pressure sensor, a pressure amplifier that amplifies pressure signals generated by the differential air pressure sensor, a microphone, a microphone amplifier that amplifies audio signals generated by the microphone, and a pulse counter that calculates a total event length. The system includes a digital processor that processes the amplified signals from the differential air pressure sensor and the microphone and a data radio that generates alerts based on input from the differential air pressure sensor and the microphone. The system determines whether a gunshot event or an explosive event has occurred based on a pressure length sensitivity setting, a microphone length sensitivity setting, and a correlation sensitivity setting.

13 Claims, 13 Drawing Sheets

(56) References Cited

U.S. PATENT DOCUMENTS

| | | |
|---|---|---|
| 8,050,141 B1 | 11/2011 | Carroll et al. |
| 8,111,582 B2 | 2/2012 | Beck et al. |
| 8,325,563 B2 | 12/2012 | Calhoun et al. |
| 2005/0237186 A1 | 10/2005 | Fisher et al. |
| 2006/0044943 A1 | 3/2006 | Barger et al. |
| 2006/0114749 A1 | 6/2006 | Baxter et al. |
| 2007/0030763 A1 | 2/2007 | Barger et al. |
| 2008/0008044 A1 | 1/2008 | Patterson et al. |
| 2008/0192574 A1 | 8/2008 | Baxter et al. |
| 2010/0142328 A1 | 6/2010 | Beck et al. |
| 2011/0069585 A1 | 3/2011 | Baxter et al. |
| 2012/0177219 A1 | 7/2012 | Mullen et al. |
| 2012/0182834 A1 | 7/2012 | Mullen et al. |
| 2012/0182837 A1 | 7/2012 | Calhoun et al. |
| 2012/0275272 A1 | 11/2012 | Mullen et al. |
| 2014/0190051 A1 | 7/2014 | Wichner |

* cited by examiner

SYSTEM AND DEVICE FOR NEARFIELD GUNSHOT AND EXPLOSION DETECTION

CROSS-REFERENCE TO RELATED APPLICATION

Pursuant to 35 U.S.C. § 119(e), this application claims priority back to U.S. Patent Application No. 62/043,515 filed on Aug. 29, 2014, the contents of which are incorporated herein by reference.

BACKGROUND OF THE INVENTION

1. Field of the Invention

The present invention relates generally to the field of gunshot and explosion detection, and more particularly, to a system and device for detecting the nearfield presence of gunfire and/or explosions by evaluating the acoustic energy and the instantaneous change of localized air pressure when a gun is discharged or an explosive device detonated.

2. Description of the Related Art

There are a number of inventions that use various typos of sensors to detect projectiles, but none of these inventions combines a microphone with a differential pressure sensor and software that enables gunshots to be differentiated from explosions and single gunshots from multiple gunshots, while at the same time minimizing false positives by differentiating explosive events from non-explosive events.

U.S. Pat. No. 5,241,518 (McNelis et al., 1993) discloses an apparatus and method for determining the trajectory of a supersonic projectile of unknown velocity and direction. The apparatus has at least throe spaced-apart sensors capable of registering a shock wave generated by a supersonic projectile passing in the vicinity of the sensors. The sensors generate signals based on the azimuth and elevation angle of a unit sighting vector from each sensor to the point of origin of the shock wave. A computer then calculates the azimuth and elevation angle of the local trajectory of the projectile.

U.S. Pat. No. 5,544,129 (McNelis, 1996) provides a method and apparatus for determining the general direction of the origin of a projectile. A sensor with three spaced-apart transducers generates signals in response to a blast wave created at an origin of a projectile. The signals generated by the transducers enable a time relation to be measured among the three transducers as the blast wave serially encounters each of the three transducers. From the time relations, a sighting vector from the sensor to the origin of the blast wave is determined.

U.S. Pat. No. 5,930,202 (Duckworth et al., 1999) and U.S. Pat. No. 6,178,141 (Duckworth et al., 2001) describe a sniper detection and localization system that uses observations of the shock wave from supersonic bullets to estimate the bullet trajectory, Mach number and caliber. The system uses a distributed array of acoustic sensors to detect the leading edge of a projectile's shock wave and the muzzle blast from a firearm. This information is then used to measure the wave arrival times of each waveform type at the sensors. This time of arrival information determines the projectile's trajectory and a line of bearing to the origin of the projectile.

U.S. Pat. No. 6,281,792 (Lerg et al., 2001) involves a system and method for detecting a firearm shot. The system uses one or more sonic sensors that sense the firearm shot and transmit a signal to a base unit that processes the signal and determines whether it represents a firearm shot. A communication device communicates to one or more entities that a firearm shot has been detected and provides an alarm indicating that the firearm shot took place.

U.S. Pat. No. 7,126,877 (Barger et al., 2006) and U.S. Pat. No. 7,408,840 (Barger et al., 2008) disclose a system and method for locating shooters of supersonic projectiles based on shockwave measurements only. The system incorporates five to seven sensors set at least one meter apart. The sensor signals are processed by computer software to generate a shockwave arrival angle unit vector. Two different methods are described; one method uses counters in each signal channel and another method uses cross-correlation between signal channels.

U.S. Pat. No. 7,266,045 (Baxter et al., 2007), U.S. Pat. No. 7,688,679 (Baxter et al., 2010) and U.S. Pat. No. 8,036,065 (Baxter et al., 2011) provide a system and method for locating and identifying an acoustic event such as gunfire. The system incorporates a plurality of person-wearable acoustic sensors, each having a display for displaying information to the user. The sensor includes a microphone, an A/D converter, a processor, a GPS receiver, and a network interface. The processor processes a digitized signal to detect a gunshot and determine a time of arrival.

U.S. Pat. No. 7,750,814 (Fisher et al., 2010) describes an acoustic sensor that can be worn by a person for detecting gunshot events. The sensor has a housing, a microphone, a processor, a GPS receiver, and a display. The sensor is either integrated into a piece of equipment normally carried by a soldier, integrated into an article of clothing, or secured to such a piece of equipment or article of clothing.

U.S. Pat. No. 8,050,141 (Carroll et al., 2011) involves a system and method for estimating a trajectory of an incoming bullet based on the acoustics of the shock wave created as the bullet travels through the air. A first auditory signal representing a direct sound from the shock wave is recorded and its azimuthal direction determined. A second auditory signal representing a reflection of the shock wave as it travels through the air is also recorded and its azimuthal direction determined. These two signals are used to determine an estimated direction of the bullet source.

U.S. Pat. No. 8,111,582 (Beck et al. 2012) covers user-wearable sensor arrays for use with projectile-detection systems. The sensor array comprises a plurality of sensors configured to detect at least one of sound waves and pressure waves caused by at least one of the muzzle blast and shockwave of a projectile and a collar that supports the sensors.

U.S. Pat. No. 8,325,563 (Calhoun et al., 2012) discloses systems and methods for locating weapon fire incidents using data from acoustic, optical, seismic and/or other sensors. The invention includes a method for locating the incident from a combination of propagation phenomena including a discharge time of the weapon fire incident. The method may include processing the data from various signals to determine the location using a common time basis among sensor measurements.

U.S. Patent Application Pub. No. 2008/0008044 (Patterson et al.) provides a system for detecting acoustic events comprising a wearable sensor with a microprocessor, a microphone communicating with the microprocessor, a GPS module, and a display screen. The microphone allows the microprocessor to detect the acoustic event, the GPS determines the location of the wearable sensor, and the system triangulates the location and time of the acoustic event to detect gunshots. A wireless network system allows for the interfacing and sharing of data between the sensor and other components of the system.

U.S. Patent Application Pub. Nos. 2012/0177219 (Mullen et al.), 2012/0182834 (Mullen et al.), and 2012/0275272 (Mullen et al.) describe a wearable shooter localization system that includes a microphone array, processor and output device. The microphone array senses acoustic events caused by gunfire and provides electrical signals to the processing unit. The system optionally includes orientation and/or motion detection sensors that are used to initially compute a direction to the origin of a projectile in a frame of reference that is meaningful to the wearer or to subsequently update that direction as the wearer moves.

U.S. Patent Application Pub. No. 2014/0190051 (Wichner) discusses an apparatus, device or method for detecting am or pointing direction of a firearm. The method involves detecting a sound signature from of a gunshot from the firearm, sensing an aim direction of the firearm at the time of the sound signal, setting a reference direction, sensing a current aim direction and comparing it to the reference direction, and initiating an alarm if the current aim direction is beyond a threshold angle of displacement from the reference direction.

Many of the prior art references discussed above, including, but not limited to, U.S. Pat. No. 7,266,045 (Baxter et al., 2007), U.S. Pat. No. 7,688,679 (Baxter et al., 2010) and U.S. Pat. No. 8,036,065 (Baxter et al., 2011), involve determining the location of the gunshot based on time difference of arrival from multiple audio sensors that are physically separated by relatively large distances. The present invention, on the other hand, is a nearfield gunshot device that utilizes a differential air pressure sensor in addition to an audio sensor (both contained within a single device) to detect gunshots and other explosive events. The system described in the Baxter patents use a call center to validate the gunshot audio signal and decide whom to contact (in other words, the system requires human intervention). Furthermore, the Baxter system requires more than one device to generate the location information (based on time difference of arrival). The present invention does not require a call center, does not depend upon time difference of arrival, and a single device is all that is needed to determine that a gunshot has occurred within proximity of the device location. As used herein, the term "nearfield" means within an enclosed room or within approximately five meters of a person wearing the device outside.

BRIEF SUMMARY OF THE INVENTION

The present invention is a computer-implemented system for nearfield gunshot and explosion detection comprising: a hardware device comprising a differential air pressure sensor, a pressure amplifier that amplifies pressure signals generated by the differential air pressure sensor, a microphone, a microphone amplifier that amplifies audio signals generated by the microphone, and a pulse counter that calculates a total event length; a digital processor that processes the amplified signals from the differential air pressure sensor and the microphone; and a data radio that generates alerts based on input from the differential air pressure sensor and the microphone; wherein the system determines whether a gunshot event or an explosive event has occurred based on a pressure length sensitivity setting, a microphone length sensitivity setting, and a correlation sensitivity setting.

In a preferred embodiment, the amplified pressure signal is transmitted to a first hardware-based root mean square detector circuit that generates a first voltage output that is transmitted to a first hardware-based envelope detector that converts the first voltage output to a first digital square pulse that is transmitted to the digital processor; and the amplified audio signal is transmitted to a second hardware-based root mean square detector circuit that generates a second voltage output that is transmitted to a second hardware-based envelope detector that converts the second voltage output to a second digital square pulse that is transmitted to the digital processor. In another preferred embodiment, when the device is powered, it undergoes a calibration process wherein the device reads a first sequence of analog microphone readings, average the readings, and notes a default baseline microphone audio level reference; wherein an internal tone generator within the device generates a tone and reads a second sequence of microphone readings and averages the readings to determine a reference level change with and without a tone present; and wherein if the microphone calibration process is successful, an initialization message is sent to an alerting server, and all system variables are reset.

In a preferred embodiment, an interrupt request process is initiated by a manual button push, a pressure-detected event, or a microphone-detected event; wherein the system identifies a first-to-occur event by determining whether the manual button push event, the pressure-detected event or the microphone-detected event occurred first and sets a flag based on the first-to-occur event; and wherein the system determines whether the manual button push event, the pressure-detected event and the microphone-detected event are inactive, and if so, calls event processing. In another preferred embodiment, the pressure-detected event has a length, the microphone-detected event has a length, and the system determines whether the length of the pressure-detected event exceeds a first predetermined value and whether the length of the microphone-detected event exceeds a second predetermined value; and the system identities either the pressure-detected event or the microphone-detected event as a last-to-deactivate event, and wherein the system determines the total event length based on activation of the first-to-occur event and deactivation of the last-to-deactivate event.

In a preferred embodiment, if the pressure-detected event occurs before the microphone-detected event, the system determines whether the microphone-detected event occurred within a predetermined period of time after the pressure-detected event occurred; and the system determines whether the length of the microphone-detected event is longer than the length of the pressure-detected event; and the system determines whether a gunshot or an explosion occurred based on the length of the microphone-detected event and the length of the pressure-detected event. In another preferred embodiment, if the microphone-detected event occurs before the pressure-detected event, the system determines whether the pressure-detected event occurred within a predetermined period of time after the microphone-detected event occurred; the system determines whether the length of the microphone-detected event is longer than the length of the pressure-detected event; and the system determines whether a gunshot or an explosion occurred based on the length of the microphone-detected event and the length of the pressure-detected event.

In a preferred embodiment, the differential air pressure sensor is a subsonic sensor. Preferably, the hardware device further comprises an absolute air pressure sensor. The hardware device preferably further comprises an accelerometer sensor. The hardware device preferably further comprises a location receiver. The hardware device preferably further comprises a manual alert button.

In a preferred embodiment, the invention further comprises a multiple gunshot window timer that determines whether an event is a multiple shooting event. In another preferred embodiment, the invention further comprises a gunshot counter that determines the number of gunshots detected within a window timer period.

DETAILED DESCRIPTION OF INVENTION

A. Overview

Figure 1:
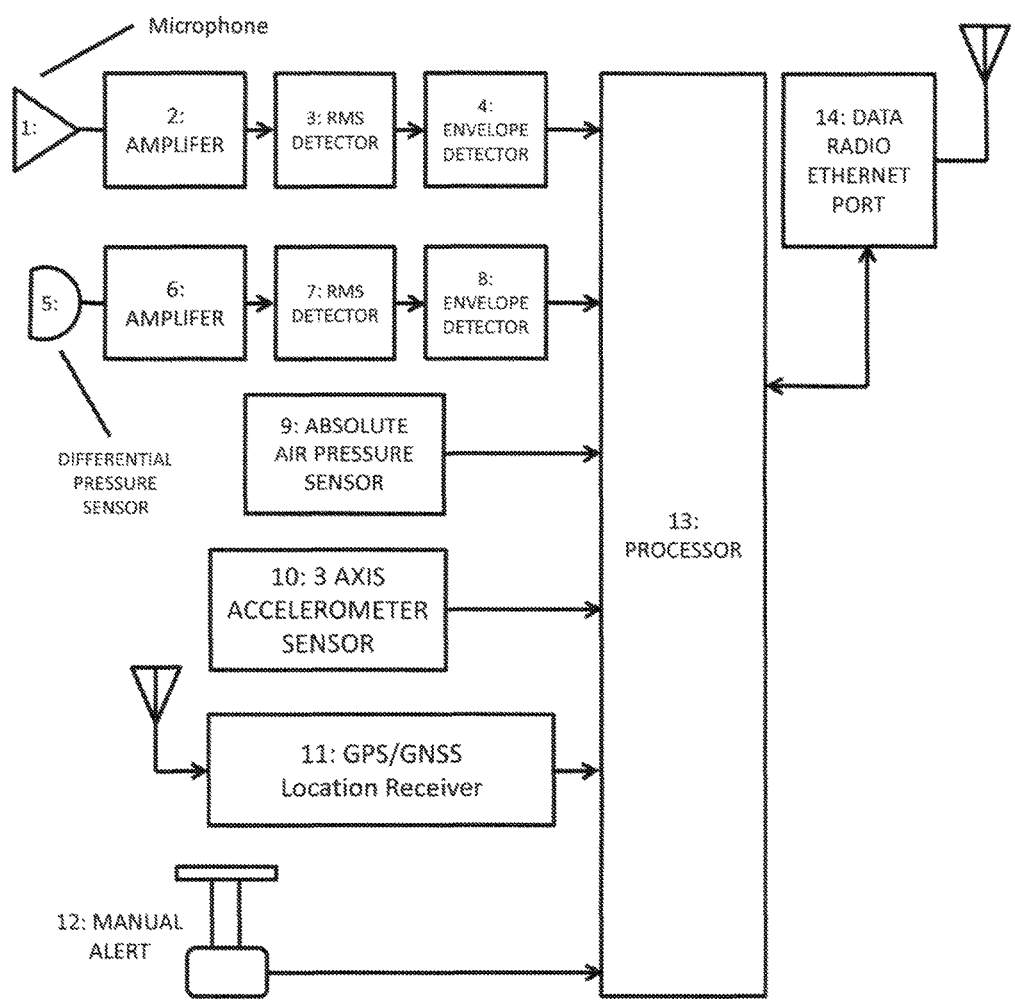
FIG. 1 is a diagram of the system architecture of the present invention.

The present invention was designed and developed to address the issue of response time when a gun shooting (or explosive event) occurs indoors or outdoors. The industry average response time is 18 minutes from the shooting to the arrival of the first responders. During these critical minutes, lives are at stake, and valuable information is inevitably lost. The present invention solves this problem by providing an automated method of detecting a gunshot or explosion, identifying the location, and providing this and other sensor information within seconds to law enforcement, school resource officers and other intended persons. The data is transmitted using wireless communications such as cellular or Wi-Fi. The indoor model of the present invention also provides a contact closure indication to the building's integrated alarm system. If a data network is not available, then the present invention is configured to interface with the building's alarm system to alert the appropriate personnel of the event.

A significant problem associated with existing technologies is the generation of false positives, which are indications that a gunshot was detected when in fact it was not. The present invention overcomes this disadvantage by utilizing several sensors to validate the gunshot with a high level of certainty. The present invention detects both the acoustic indication and the air pressure changes that happen when the gunpowder explosion occurs. These two key indicators enable the present invention to differentiate between a gunshot and a loud noise.

Once these two critical pieces of information are detected and the timing associated with the events is measured, the present invention will indicate that a gunshot has occurred. Detection of the initial gunshot starts a windowing function that provides a method of determining whether the detected event is a single gunshot or multiple gunshots. By informing first responders as to whether there has been a single shot or multiple shots, the present invention allows those responders to gauge the magnitude of the event before arriving on the scene. In addition to the shot counter, the present invention includes functionality that assesses the different characteristics of multiple gunshots; this functionality enables an approximation of the number of shooters and/or different types of weapons. By cataloging and comparing the specific traits (including pressure, microphone and vibration) of which each shot is comprised, when another gunshot/explosion or event occurs within the same shooting event, (defined as detected gunshots or explosions that occur within the Multiple Gunshot Window Timer), the invention can determine whether more than one type of weapon is used. If the specific traits are different, then the invention indicates that there may be two shooters or multiple weapons used in the detected event.

In sum, the present invention is intended to provide as much metric data associated with an event as possible, in a quick and accurate manner. The main advantage of the present invention is that it provides an automated alerting technology that will save lives. Lowering the response time decreases the loss of life from gunshot and explosion events. In a preferred embodiment, a single gunshot will generate one type of alert, multiple gunshots will generate another type of alert, and the manual alert (which is triggered by a button on the device) will generate a third type of alert. The same technology is used to generate the alert in all cases.

B. Detailed Description of the Figures

The present invention is comprised of several hardware and software elements that enable the functionality described herein. Referring to FIG. 1, the system uses a microphone (FIG. 1:1) to listen to the audio portion of the event, a microphone amplifier (FIG. 1:2) to amplify the microphone's audio level and a differential air pressure sensor (FIG. 1:3) to feel the air concussion that occurs when a gun is fired or an explosive device is detonated. Note that many of the prior art references discussed above incorporate sonic sensors. The present invention does not use sonic sensors, and the differential air pressure sensor of the present invention is a subsonic sensor.

In a preferred embodiment, the microphone is a ceramic condenser element; this type of element is preferred because of its flat audio response. The audio signal from the microphone is amplified (FIG. 1:2) before feeding the hardware based RMS (root mean square) detector (FIG. 1:3). An RMS detector is used to create an envelope that provides a DC (direct current) voltage of all of the audio frequencies within the envelope of the detector and to provide a full-response detection of the incoming analog envelope within 40 milliseconds (mS). The RMS detector output feeds a hardware-based envelope detector (FIG. 1:4) utilizing a precision wide-temperature reference voltage that converts the RMS voltage output into a digital square pulse that is transmitted to the digital processor (FIG. 1:13).

The differential air pressure sensor (FIG. 1:5) is used to measure the fraction of a second increase in air pressure that happens when an explosion (caused by either a gunshot or an explosive device) occurs. Both elements—the microphone and the differential air pressure sensor—are required for the invention to operate properly. The pressure signal from the pressure sensor is amplified (FIG. 1:6) and then transmitted to the hardware-based RMS detector circuit (FIG. 1:7). An RMS detector is used to create an envelope that contains a DC voltage of the pressure-induced pulse wave and provides a full-response detection of the incoming analog envelope within 40 mS. The RMS detector output feeds a hardware-based envelope detector (FIG. 1:8) utilizing a precision wide-temperature reference voltage that converts the RMS voltage output into a digital square pulse that is transmitted to the digital processor (FIG. 1:13).

The absolute air pressure sensor (FIG. 1:9) is used to measure the height above the ground. The main purpose of this sensor is to determine the floor on which the sensor is located when the sensor is worn by a moving object (such as a person). The absolute air pressure sensor is not used to detect gunshots but simply to monitor vertical position.

The hardware portion of the invention can be embodied in two physical forms. The first embodiment is a fixed installation (such as a classroom or office or even an outdoor setting), and the second embodiment is a mobile device that is worn on or affixed to a moving object (such as a vehicle or a person). The two physical embodiments of the invention enable detection and reporting in multiple environments (such as an officer discharging his weapon in the field or a school shooting in a classroom).

The purpose of the accelerometer sensor (FIG. 1:10) is to detect movement of a moving object and to monitor and correlate the impact concussion from a gunshot or explosive event. The information obtained from this sensor is used in conjunction with the differential pressure sensor during a detection event to provide individuals receiving the alerts with additional information about the wearer of the device (e.g., whether the person is moving).

The location receiver (FIG. 1:11) is used to provide the location of the detector when GPS (global positioning system) and GNSS (global navigation satellite system) are available. This sensor is used to identity the location of the device when the hardware is in the form of a fixed installation, and this information is preferably provided to the individuals receiving the alerts.

The manual alert button (FIG. 1:12 is used to manually initiate an alert by the detector when an event takes place requiring manual intervention. It is possible, within the context of the present invention, for a manual alert to be transmitted without a gunshot being detected. In one embodiment of the hardware device (where the hardware device is a mobile device), the manual alert button is preferably located on the top of the device so that the individual wearing the device can press the manual alert without needing to look for the button. In another embodiment of the hardware device (where the hardware device is a fixed installation, for example, on the wall of a classroom), the manual alert button may be located on the hardware device itself or remotely from the hardware device so that a person can activate the manual alert at a location different from where the shooting event may be taking place.

The system processor (FIG. 1:13) analyzes and reacts to the signals during an event. These signals include all of the signals generated by the various sensors contained within the device, namely, the differential air pressure sensor, the microphone, the absolute air pressure sensor, the accelerometer, the location receiver and the manual alert.

The data radio (FIG. 1:14) is used to alert when an event is detected. The present invention is not limited to any particular type of data radio; the data radio is any device that transmits data. In lieu of a data radio, an Ethernet port or serial port may be used.

Figure 2:
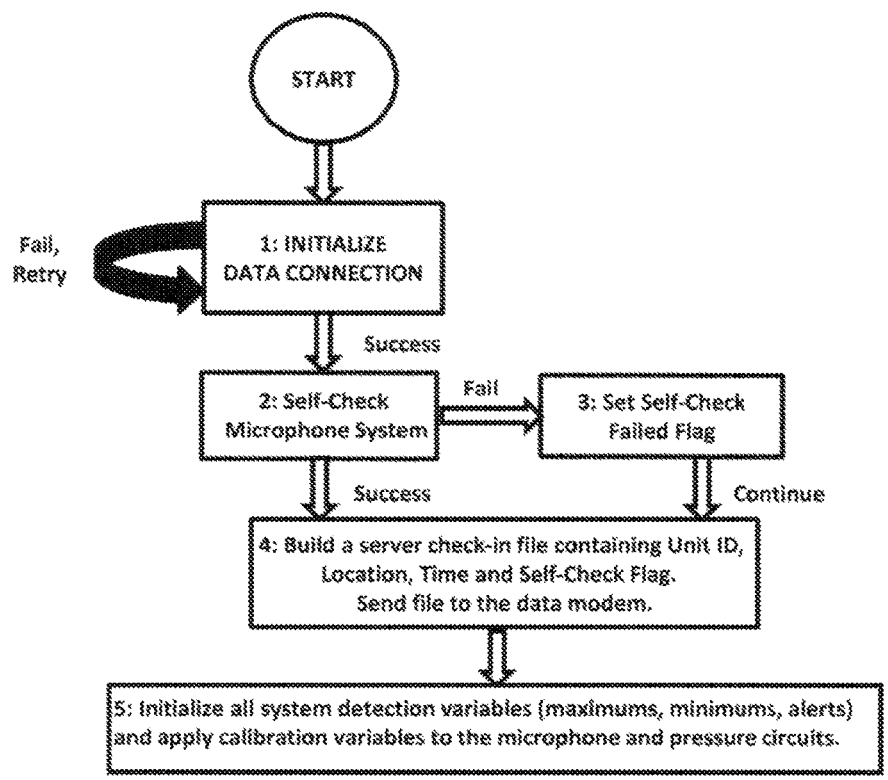
FIG. 2 is a flow diagram of the system startup sequence.

When power is removed from the device, the unit is static, and no processes are running; however, once the unit is powered, it begins the process of preparing a data connection and readying itself for monitoring. FIG. 2 outlines the process of initialization. The initial step is to verify that a data connection exists because without such a connection, no alerting is possible. FIG. 2:1 is the initialization of a data connection. The system hangs and continues to attempt a connection within the parameters of the data provider. Once successful, the system proceeds to FIG. 2:2, which is a self-test of the microphone system used as part of the event validation process. The device reads a sequence of analog microphone readings (with the tone generator disabled), averages them, and notes the default baseline microphone audio level reference. The process then generates a tone from the internal tone generator and reads a sequence of analog microphone readings (with the tone generator enabled) and averages the readings to determine the reference level change with and without a tone present. If no difference is noted, FIG. 2:3 (which indicates a microphone system calibration failure) is executed, but the system will continue to operate without a calibrated microphone system. A failed flag is set and is sent with every data packet that is relayed over the data connection. If the microphone self-test passes (i.e., if the microphone calibration process is successful), the success flag is set, and FIG. 2:4 (which builds an initial power-on check-in message) is initiated. The initialization message contains critical information about the system, including location, time at which the unit was powered on, and microphone calibration reading. The message is passed to the data modem to be sent to the alerting server for record keeping. Once the message is sent, FIG. 2:5 (which resets all system variables, including, but not limited to, maximum and minimum readings, and all operation variables to the power on-state) is initiated.

Figure 3:
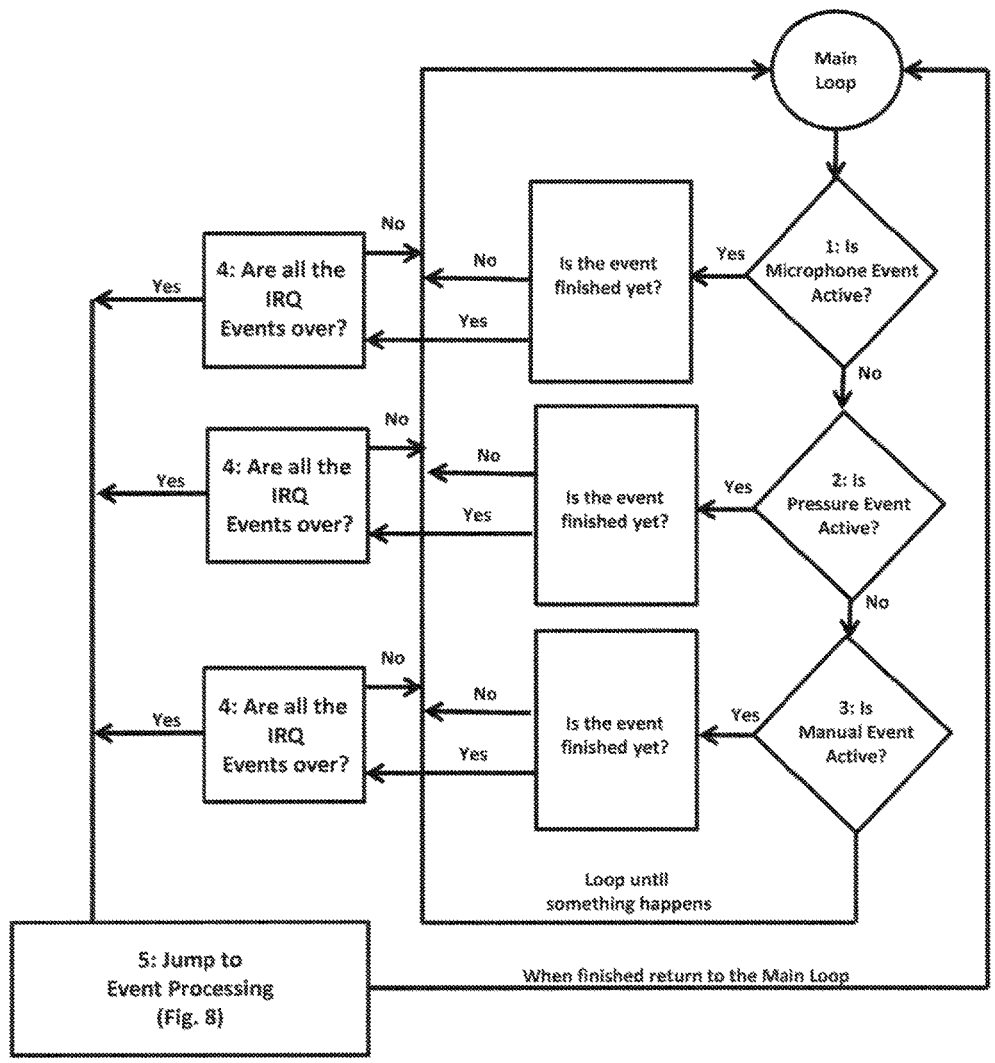
FIG. 3 is a flow diagram of the main system loop.

For efficient operation, the system is a main loop where time-critical alerts and events are internet-driven background events and polling of events status is a main loop event. FIG. 3 outlines the main loop basic operation. All events are initiated by the background interrupt process as outlined in FIG. 4 with the ending of the event polled by the main loop. This process ensures the most accurate timing of the event without compromising program latency introducing timing errors. Note that "IRQ" in FIG. 4 stands for "interrupt request."

Figure 4:
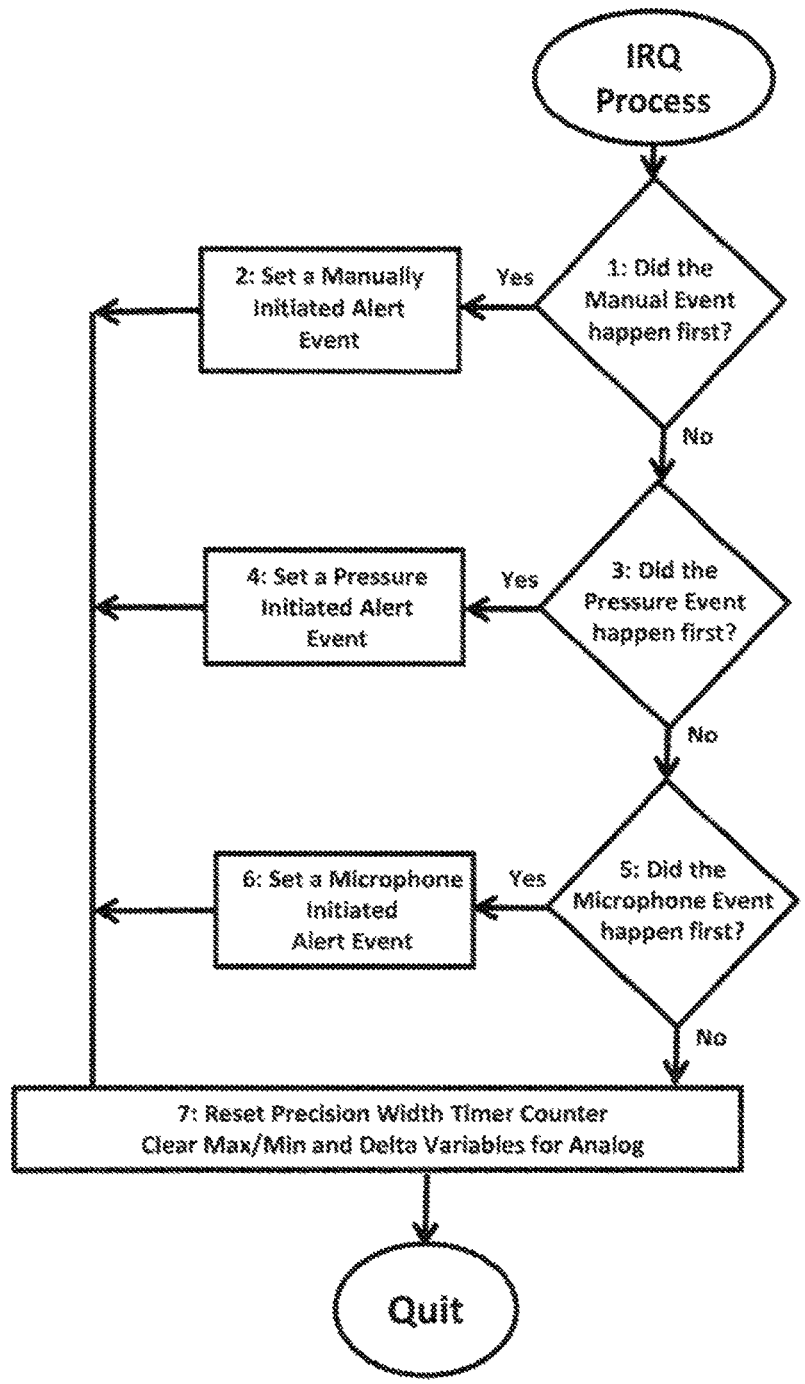
FIG. 4 is a flow diagram of the background interrupt process.

FIG. 4 outlines the IRQ process, an event-initiated process that does not run unless an event occurs. The three events that initiate an IRQ process are a manual button push (FIG. 4:1), a pressure-detected event (FIG. 4:3) and a microphone-detected event (FIG. 4:5). When one of these three events happens, the IRQ process (FIG. 4) starts. It is possible for all three events to happen, but not at the same time. When a manual event happens (FIG. 4:1), the IRQ process tests to see if it is the first event and if it is, proceeds to set the manual event happened first flag (FIG. 4:2). When a pressure event happens (FIG. 4:3), the IRQ process tests to see if it is the first event, and if it is, proceeds to set the pressure event happened first flag (FIG. 4:4). When a microphone event happens (FIG. 4:5), the IRQ process tests to see if it is the first event, and if it is, proceeds to set the microphone event happened first flag (FIG. 4:6). Once the first event has been identified and marked (FIG. 4:2 or FIG. 4:4 or FIG. 4:6), the IRQ process resets (FIG. 4:7) the pulse counter (FIG. 11:6) and other variables associated with the new event and quits. Events that happen but are not the initial event simply quit without affecting any system variables.

When an event happens that causes the external sensors to react by stimulating the microphone (FIG. 1:1 and FIG. 1:2), the RMS detector (FIG. 1:3) responds by creating a voltage from the microphone's detected audio, which causes the envelope detector (FIG. 1:4) to generate a digital pulse that corresponds to the envelope of audio from the RMS detector. The digital pulse is transmitted to the DSP processor (FIG. 1:13), which initiates an IRQ process to start (FIG. 4). This event is monitored by the main loop (FIG. 3).

Referring to FIG. 3, the main loop polls events to see whether the event is active and, if it is active, when it finishes. As used herein, the term "event" means a detected gunshot or other explosive event or the initiation of a manual alert. When all of the envelope detectors (audio and differential pressure and, if applicable, manual alert) are inactive, the event is deemed to be finished. FIG. 3:1 evaluates whether a microphone event was detected, and if so, whether it has finished. If the microphone event has not finished, then the system returns to the main loop. FIG. 3:2 evaluates the pressure event in the same manner as the microphone event, and FIG. 3:3 evaluates the manual alert button event by determining whether the event has finished. Once all the events have finished (i.e., all events are inactive), then the event processing is called. The event processing uses the first event to determine the microphone/pressure verses pressure/microphone processing (as described further below in connection with FIG. 5). Once the event order is determined (FIG. 3:4), all events must complete before the event processing begins (FIG. 3:5).

Interrupt events are processed based on the beginning edge of the event (when the envelope detector activates). The interrupt processing determines which event happened first, clears the critical timing system (see FIG. 11), and exits. Once all interrupts are finished, the system is evaluated as described in FIG. 5. To increase accuracy, all timing parameters are clocked with hardware as outlined in FIG. 11; therefore, any delays in the processing caused by software will not affect the precision of the event measurement.

Figure 5:
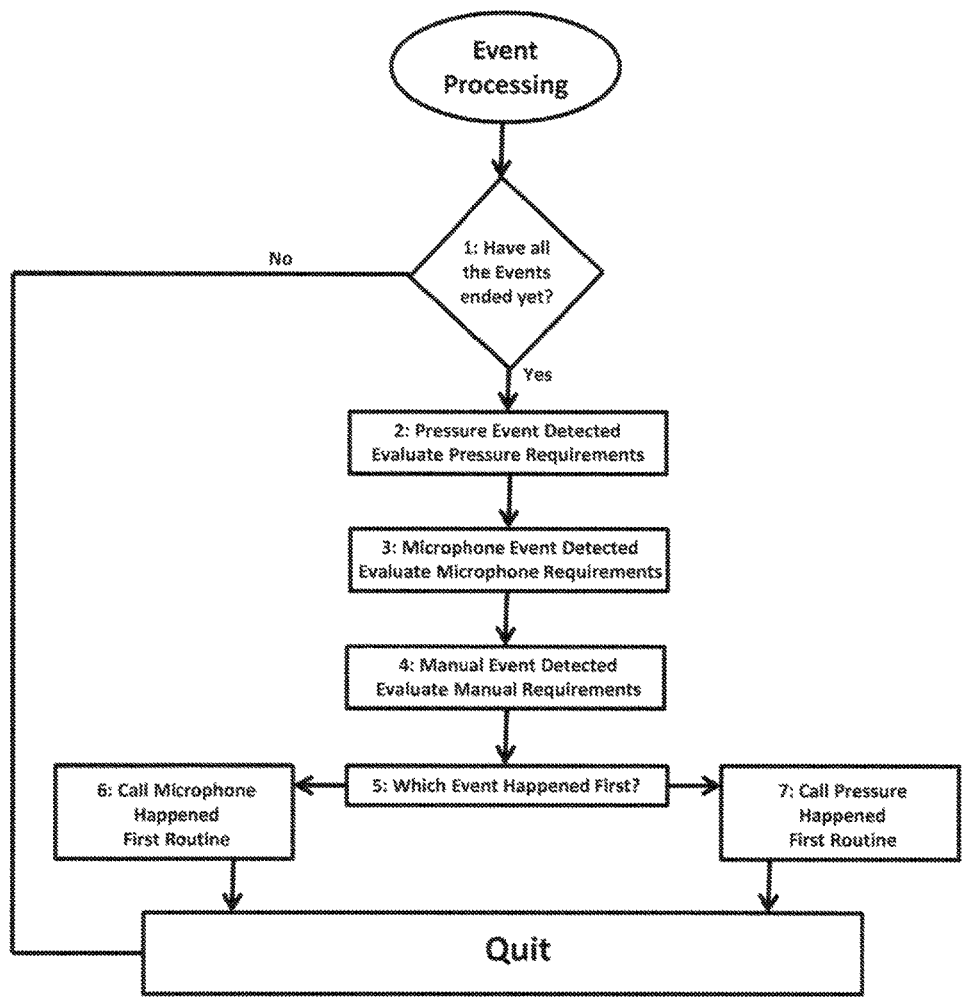
FIG. 5 is a flow diagram of the event processing routine.

Referring to FIG. 5, events are processed based on which event happened first. This is important because the order of events determines the timing parameters that are used to determine the validity of the event. The event processing (FIG. 5:1) will not begin until all events are finished. Once the events are finished, the processing of the events begins. The first step in the evaluation process is to collect the timing and analog information associated with the pressure event (FIG. 5:2). The second step in the evaluation process is to collect the timing and analog information associated with the microphone event (FIG. 5:3). The third step in the evaluation process is to analyze the timing and analog information associated with the manual event (FIG. 3:4), if applicable. Once all the data is collected, then the system determines which event happened first (FIG. 5:5). Based on the flag that was set in the interrupt process (FIG. 4), the event processing routine will execute either the microphone (FIG. 5:6) or pressure (FIG. 5:7) event first.

Figure 6:
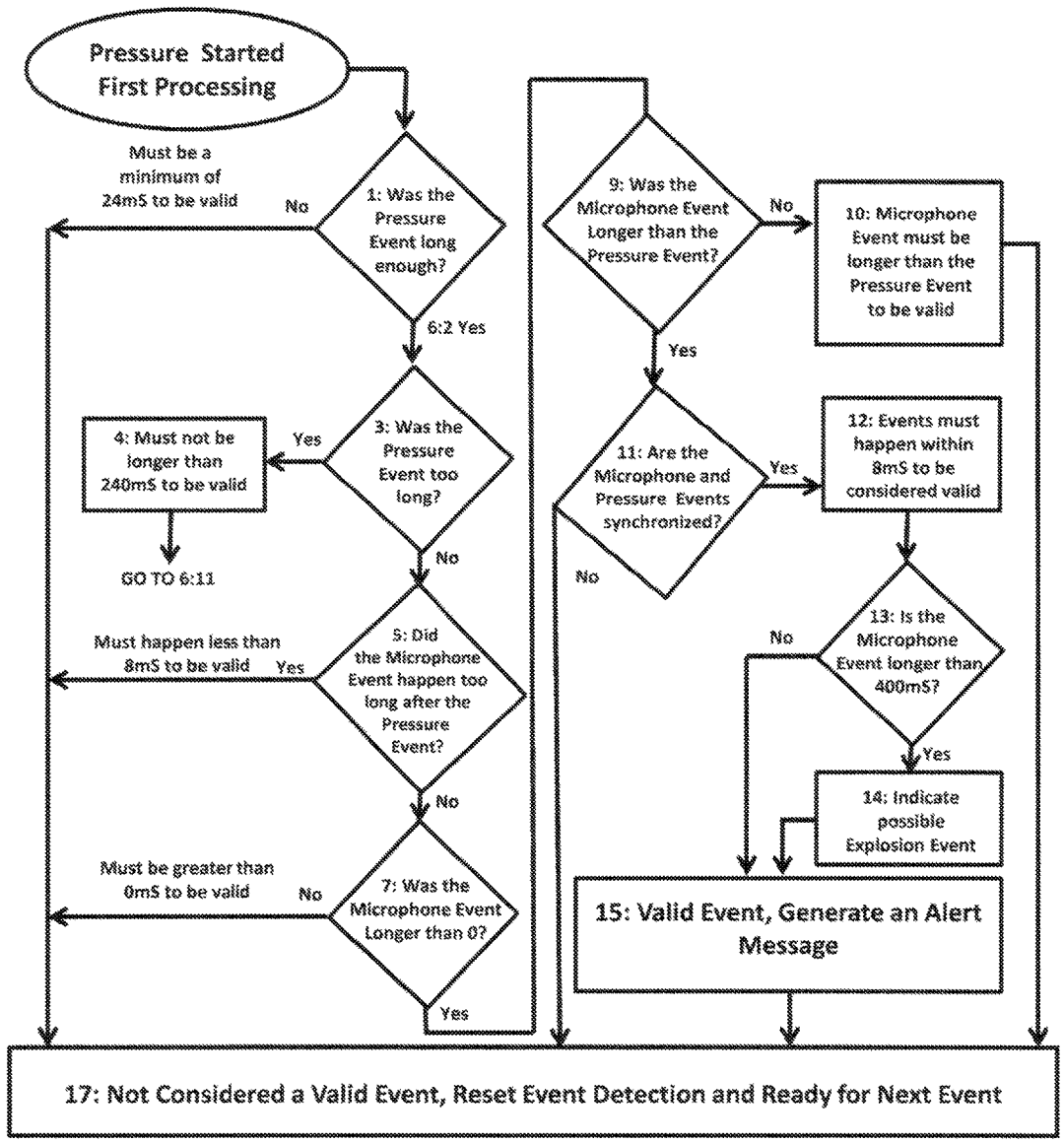
FIG. 6 is a flow diagram of the pressure event happened first routine.

FIG. 6 outlines the process that occurs when a pressure event precedes a microphone event. There are a variety of timing fields that are used to determine the validity of the event, and the values used to determine the validity of the event (as explained more fully below) can be changed to fine tune the sensitivity of the detection algorithm. The first variable that is used is the length of the pressure event (FIG. 6:1); if the event is not long enough, then the system discards the event. In a preferred embodiment, pressure must be a minimum of 24 mS in order for the event to be treated as valid (FIG. 6:2) with sensitivity settings ranging from 8 mS to 40 mS (the lower number being more sensitive and the larger number being less sensitive). The term "correlation sensitivity setting" means the range within which the audio event must occur after the pressure event. The sensitivity settings are used to validate the event, that is, determine whether the event is a gunshot or other explosive event.

The length of the pressure event is directly related to the amplitude of the air pressure wave based on the proximity of the gunshot to the differential air pressure sensor. Once the pressure event is determined to be long enough (FIG. 6:1), the pressure event is checked to determine if the event is too long (FIG. 6:3). If the event is too long as determined by the pressure event length exceeding 240 mS (FIG. 6:4), an explosive event test is performed after all other validation tests are passed (FIG. 6:11). If the pressure event is longer than 240 mS (FIG. 6:4) and the microphone event is longer than 400 mS (FIG. 6:13), and the two events pass all other testing outlined in FIG. 6, then it is determined to be an explosive event (FIG. 6:14).

If the pressure event not too long (FIG. 6:3), the microphone event is then tested (FIG. 6:5), and if the event is not long enough, then the system discards the event. In a preferred embodiment, the microphone event must be a minimum of 40 mS to be treated as valid (FIG. 6:5) with sensitivity settings ranging 25 mS to 80 mS. The term "microphone length sensitivity setting" means the actual length of the audio event. The length of the microphone event is directly related to the amplitude of the sound based on the proximity of the gunshot to the microphone.

Figure 12:
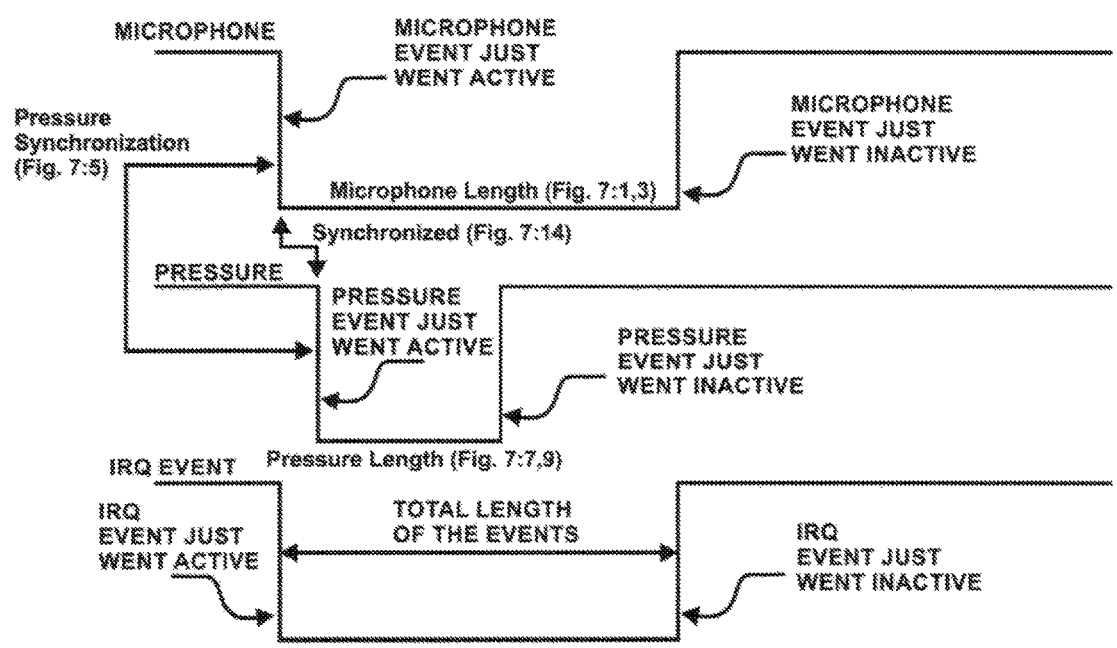
FIG. 12 is a microphone length sensitivity timing diagram.

FIG. 12 is a microphone length sensitivity timing diagram that shows how the microphone length sensitivity setting is used to validate a gunshot or explosion event. The top part of this diagram identifies what happens when the microphone detector goes active (transitions from high to low). All processes are activated on the high-to-low transition of the microphone detector. The middle part of the diagram identifies what happens when the pressure detector goes active (transitions from high to low). Note that pressure is used to validate the occurrence of a gunshot/explosion event regardless of whether the microphone event goes active first (as in FIG. 12) or the pressure event goes active first (as in FIG. 13). The bottom part of the diagram illustrates the total length of the interrupt event. The total length of the interrupt event is determined based on the last event to transition from the active state (low) to the inactive state (high). In FIG. 12, the microphone event is the first to go active and the last to go inactive; therefore, the total event length is the length of the microphone event.

Figure 13:
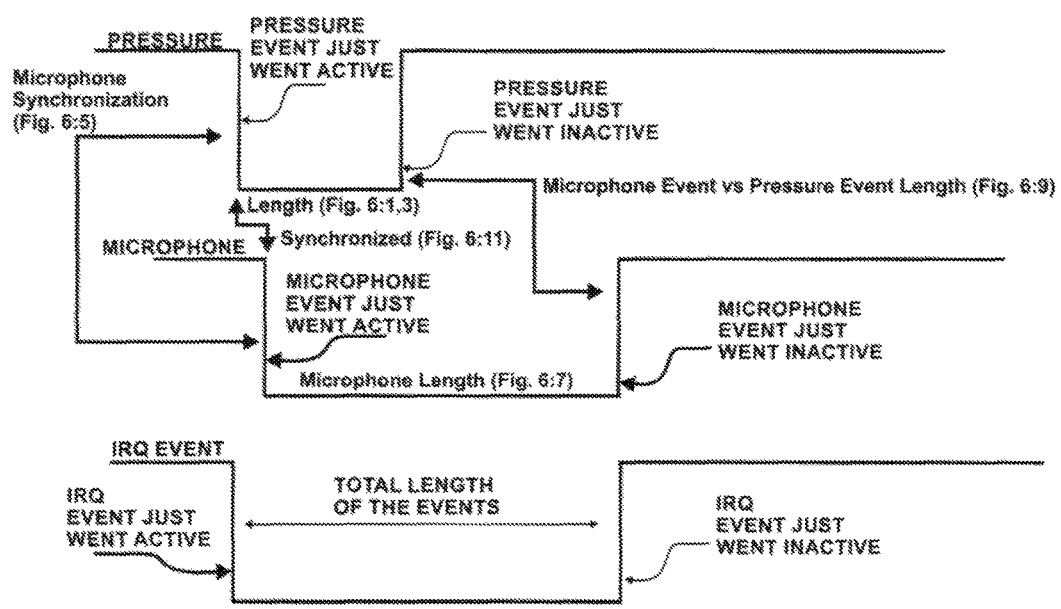
FIG. 13 is a pressure length sensitivity timing diagram.

FIG. 13 is a pressure length timing diagram that shows how the pressure length sensitivity setting is used to validate a gunshot or explosion event. The term "pressure length sensitivity setting" means the actual length of the pressure event. The top part of this diagram identifies what happens when the pressure detector goes active (transitions from high to low). All processes are activated on the high-to-low transition of the pressure detector. The middle part of the diagram identifies what happens when the microphone detector goes active (transitions from high to low). As noted above, pressure is used to validate the occurrence of a gunshot/explosion event regardless of whether the microphone event or the pressure event goes active first. The bottom part of the diagram illustrates the total length of the interrupt event. The total length of the interrupt event is determined based on the last event to transition from the active state (low) to the inactive state (high). In FIG. 13, the pressure event is the first to go active, but the microphone is the last to go inactive; the total event length is the length from the beginning of the pressure event to the end of the microphone event.

Referring back to FIG. 6, once the microphone event is determined to be long enough, the system checks to see if the microphone event happened too long after the pressure event started (FIG. 6:5). If the microphone event happened more than 8 mS after the pressure event started, then it is assumed that the events are not synchronized and are not accepted. The timing variable used in this step assumes that the air concussion and the microphone audio should be closely synchronized. In most cases, the pressure event happens first because the explosion from the gun happens before the audio from the explosion is heard, which accounts for the difference in timing. Allowing a long time between pressure and microphone events increases the possibility of false positives being detected; for this reason, the synchronization of the two events is important.

Figure 9:
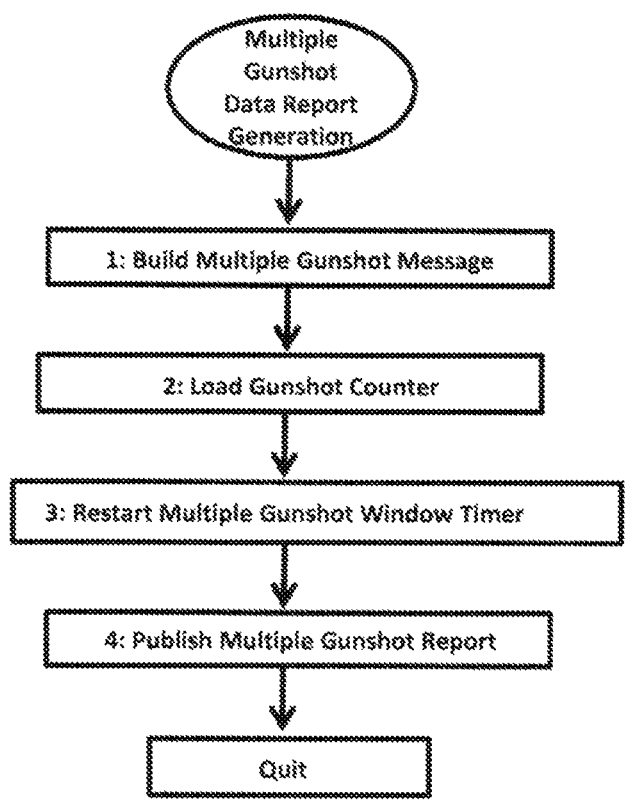
FIG. 9 is a flow diagram of the process for generating a multiple gunshot alert message.

At FIG. 6:7, the system checks to make sure the microphone event was longer than 0 because a pressure-only event is a guaranteed false positive. The next step in the validation process is to make sure the microphone event was longer than the pressure event. The microphone is more sensitive than the differential pressure sensor; therefore, to be considered valid, the microphone event must be longer than the pressure event (FIG. 6:9). Once the evaluation is completed, the system verifies that the processes are synchronized by verifying that the pressure event happened slightly before the microphone event (FIG. 6:11) (referring to the correlation sensitivity discussed in the immediately preceding paragraph) before generating a gunshot valid message. The steps shown in FIGS. 6:10 and 6:12 result in the detection system being reset (FIG. 6:14) because the detection criteria failed the necessary tests. FIG. 9 (discussed below) outlines the process of building a data message to indicate a gunshot was detected.

Figure 7:
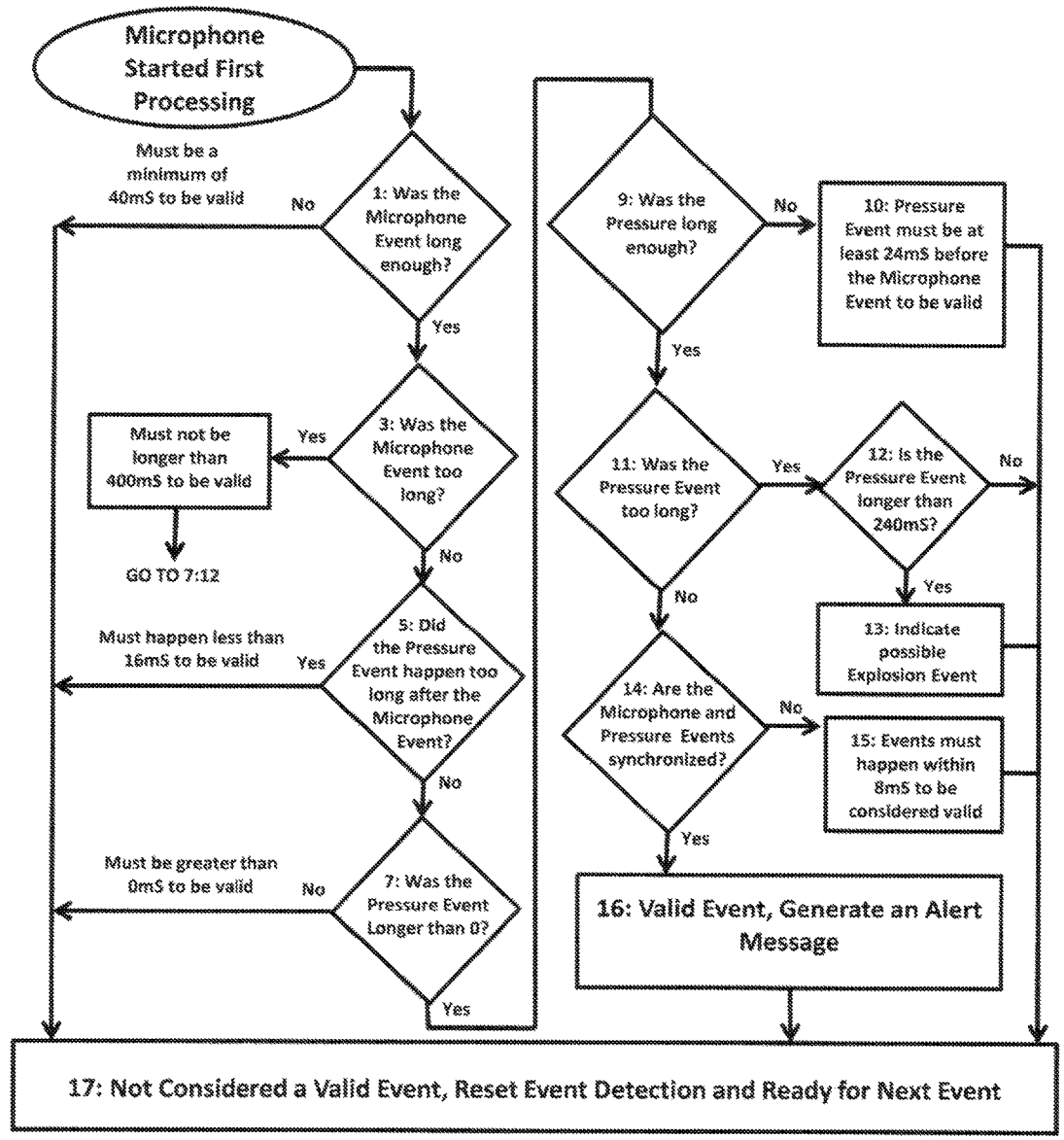
FIG. 7 is a flow diagram of the microphone event happened first routine.

FIG. 7 outlines the process that occurs when a microphone event precedes a pressure event. There are a variety of timing fields that are used to determine the validity of the event, and these values can be changed to fine tune the sensitivity of the detection algorithm. The first variable that is used is the length of the microphone event (FIG. 7:1). If the event is not long enough, then the system discards the event. The microphone event must be a minimum of 40 mS to be treated as valid (FIG. 7:2) with microphone length sensitivity settings ranging from 25 mS to 80 mS (the lower number being more sensitive and the larger number being less sensitive). The length of the microphone event is directly related to the amplitude of the sound of the event based on the proximity of the gunshot to the microphone. The microphone event is tested to make sure it is not too long, which would result in a false positive. The microphone event must be less than 400 mS to be accepted as a gunshot with longer events being treated as a possible explosive event (FIG. 7:3). If the microphone event is longer than 400 mS, then the pressure event is tested to see if it was longer than 240 mS (FIG. 7:12). If the pressure event is longer than 240 mS, then the event is assumed to be an explosion.

If the microphone event is determined to be long enough, then the pressure event is tested (FIG. 7:5). If the pressure event happened too long after the microphone event, then both events are assumed to be invalid. The correlation sensitivity setting associated with the pressure/microphone events defaults to 16 mS. If the correlation sensitivity setting is too large, then the possibility of a false positive will increase because the events may not be related. The timing variable used in this step assumes that the air concussion and the microphone audio should be closely synchronized. The pressure event normally, but not always, occurs first with larger caliber guns, the pressure event might not occur before the microphone event.

At step 7:7, the system checks to make sure the pressure event was longer than 0 because a microphone-only event is a guaranteed false positive for a nearfield gunshot event. The pressure component is important to validate the microphone audio that is detected because in most circumstances an audio-only event will be assumed invalid. The next step in the validation process is to make sure the pressure event was long enough (FIG. 7:9); a preferred minimum length is 24 mS. Making this variable shorter increases the sensitivity and longer decreases the sensitivity. If the pressure is too short, the system will be more prone to false positives. The next step in the validation process is to make sure the microphone event was not too long for a gunshot (FIG. 7:11). If the pressure event is longer than 240 mS, and the microphone event is longer than 400 mS, an explosion is assumed (FIG. 7:13). If the pressure is not too long (FIG. 7:11), the last stage of the validation is to verify that the events are synchronized (FIG. 7:14). The microphone and pressure events must be synchronized within 8 mS to be considered valid before generating a gunshot valid message. The steps shown in 7:10, 7:12 and 7:15 all result in the detection system being reset (FIG. 7:17) because the detection criteria failed the necessary tests.

Figure 8:
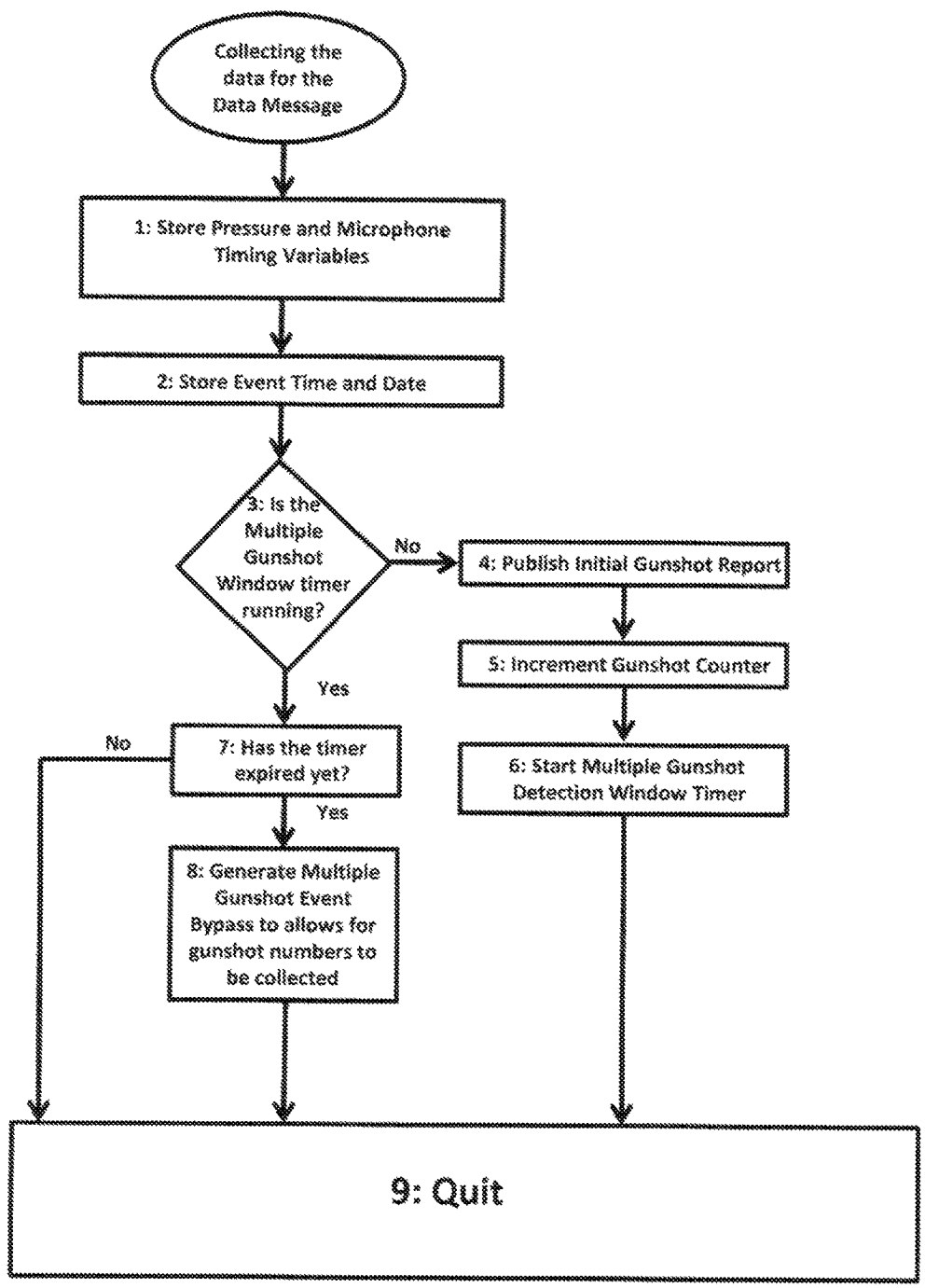
FIG. 8 is a flow diagram of the process for generating an event-based alert message.

Referring to FIG. 8, once an event has been validated, a call-out data message is generated. When an event takes place, the pressure and microphone data is stored so that when it is time to compile a message, the data will be correct as of the moment when the event occurred as opposed to when the compiled message is built (FIG. 8:1). The data includes all of the variables for pressure event length, microphone event length, and the timing between the events. Next, the system recalls the time/date of the event to include this information in the compiled message (FIG. 8:2). The time/date is when the event was validated, not when the event was compiled. The next step is to determine if this is the initial event or a follow-up multiple gunshot event (FIG. 8:3). The software tests to see if the multiple gunshot window timer (FIG. 8:6) is running, and if not, then it is the initial event (FIG. 8:4), which is followed by incrementing the gunshot counter (FIG. 8:5) and restarting the multiple gunshot window timer (FIG. 8:6). If the timer is already running, then a previous event has occurred, which indicates that the situation is a multiple shooting event (FIG. 8:7). If the event is determined to be a multiple shooting event, then the sending of the data is delayed to allow the window timer to generate a complete view of the shooting event. The system generates a message bypass condition (FIG. 8:8) to allow for the counting of multiple gunshots (i.e., the system does not reset until a certain period of time after the initial gunshot).

If this is the initial gunshot event (FIG. 8:3 failed the multiple shooting test), then an initial gunshot report is generated (FIG. 8:4). Once this report is generated, then the gunshot counter is incremented (FIG. 8:5), and the multiple gunshot window timer is started (FIG. 8:6). In a preferred embodiment, the default length of the multiple gunshot timer is 60 seconds because it is assumed that a multiple shooting event would be concluded within this time frame and also because it is presumed to be a long enough period of time to give the responders a more accurate view of the size of the event.

Referring to FIG. 9, if multiple shots are detected, the multiple gunshot window timer is started and defaults to 60 seconds. When the 60-second timer expires, the routine shown in FIG. 9 is started. This routine is only called if multiple gunshots are detected while the window timer is running. Assuming multiple gunshots have been detected, once the window timer expires (FIG. 8:8), a multiple gunshots message is built and sent. At step FIG. 9:1, the system builds a message indicating that a multiple gunshot event has been detected, loads the gunshot counter (FIG. 9:2), and inserts the count into the message. At step FIG. 9:3, the system restarts the 60-second gunshot window timer to collect additional gunshot reports within another window period. Finally, the message is published to the data modem (FIG. 9:4), and the routine quits. Once the multiple gunshot window is running, the system starts watching the event (FIG. 10), and the need to continue sending multiple gunshot messages is determined.

Figure 10:
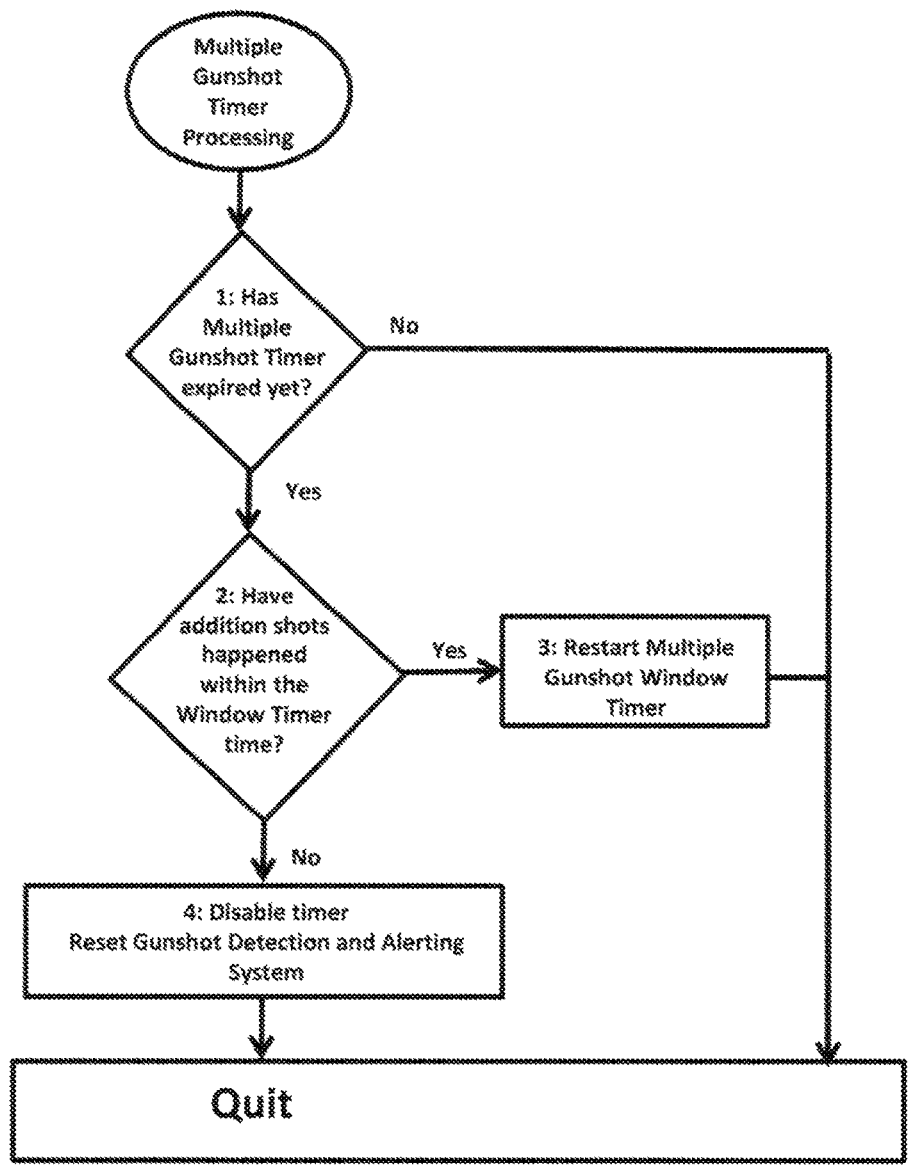
FIG. 10 is a flow diagram of the multiple gunshot timer.

After a single gunshot is detected, the multiple gunshot window timer is started (FIG. 8:6). The main process watches the window timer to determine if a multiple gunshot event has taken place (FIG. 10:1). Once the window timer has expired, the routine loads the gunshot counter to determine if any additional gunshots have been detected within the window timer period (FIG. 10:2). If no additional shots have been counted, then the window timer is disabled and the gunshot system reset (FIG. 10:4) to the starting point (FIG. 2:5). If additional gunshots are detected, then the multiple gunshot window timer is restarted (FIG. 10:3).

Figure 11:
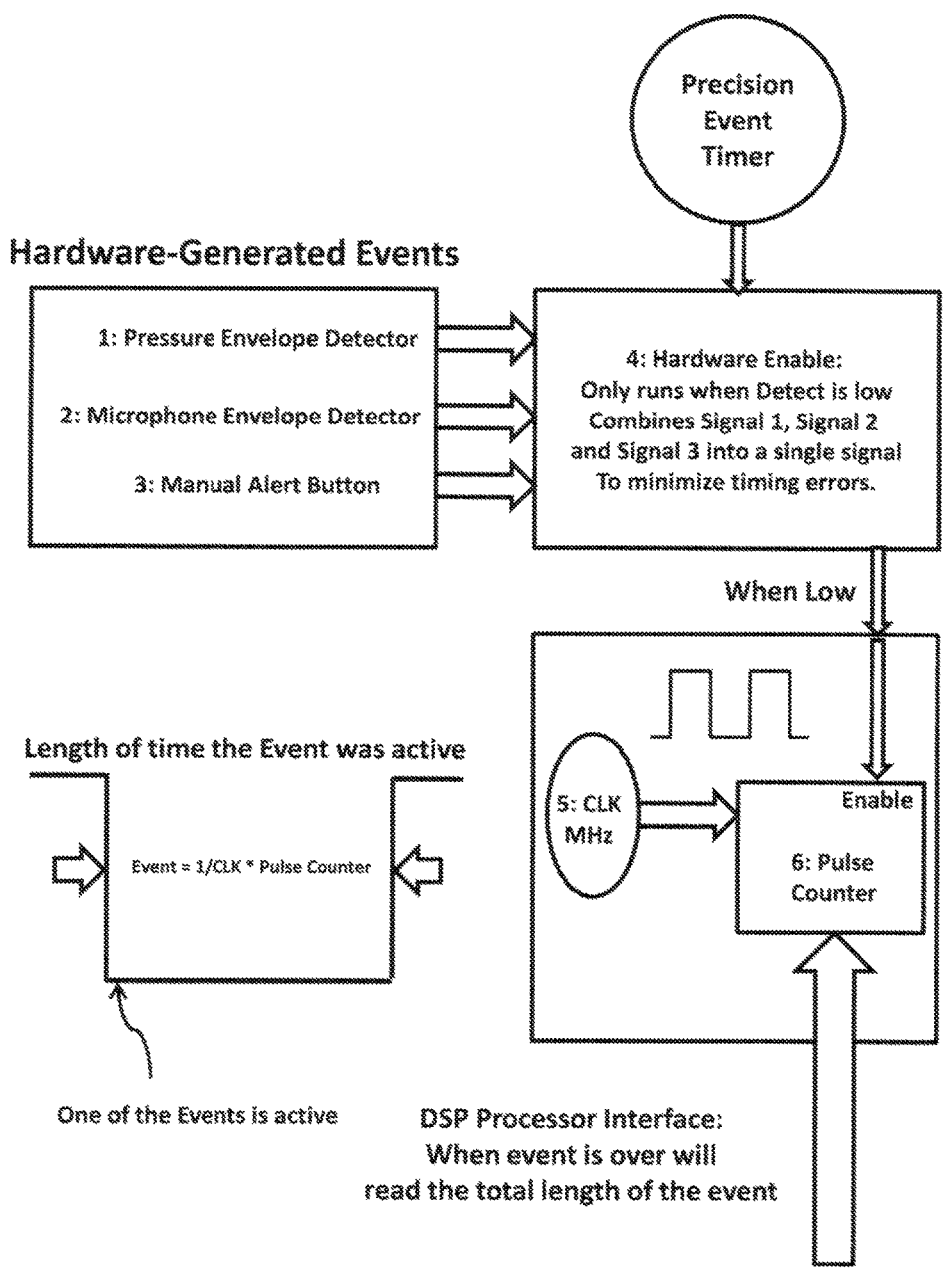
FIG. 11 is a flow diagram of the precision event width timer.

The present invention includes a pulse counter as part of the digital processor hardware. The pulse counter functions as the master counter for all events and resets itself to allow repeated detection of events. FIG. 11 shows how the three types of events—pressure (FIG. 11:1), microphone (FIG. 11:2) and manual (FIG. 11:3)—are used to enable the hardware pulse counting of the combined events. The three external hardware detect signals are combined into a single signal that controls the pulse counter so that a single interrupt signal is provided to the digital processor. By using a single combined signal, the error in timing that can result with three signals activating the digital processor at similar times is removed from process by having only one timing critical signal, (FIG. 11:4). The combined signal is used to enable the pulse counter (FIG. 11:6). The hardware inputs that enable the pulse counting are considered active when they are low (digital 0). In the hardware, the three external events that enable counting (manual pressure and microphone) are combined so that if any one of the inputs is active (digital 0), the counter is enabled to count.

The pulse counter total length is a combined total of the length of all of the events (FIG. 11:4). At the beginning of an event, when the first detected signal (microphone, differential pressure or manual-initiated signal) goes active, the pulse counter is reset to all zeroes so that the event can be accurately counted. The clock feeding the pulse counter is the master clock divided down (FIG. 11:5) to provide an eight-microsecond resolution count. As long as any of the events (manual, pressure and microphone) is active, the pulse counter will count up in eight-microsecond steps until all of the events are no longer active. The main loop (FIG. 2) of the system will determine when each of the detected events ends and records the pulse counter counts as part of the evaluation. When all of the events are finished, the system begins its evaluation process to determine if a gunshot or explosion has occurred. Every time a new event starts, the hardware pulse counter is reset. Software latency is not a factor because the signals that enable the pulse counter are strictly dependent on the hardware (i.e., there is no software processing step).

Although the preferred embodiment of the present invention has been shown and described, it will be apparent to those skilled in the art that many changes and modifications may be made without departing from the invention in its broader aspects. In addition, although the above description focuses on law enforcement and security settings, the present invention may have applicability in other settings as well. The appended claims are therefore intended to cover all such changes and modifications as fall within the true spirit and scope of the invention.

I claim:

1. A computer-implemented system for nearfield gunshot and explosion detection comprising:
    (a) a hardware device comprising a differential air pressure sensor that is configured to measure increases in air pressure that happen when a gun is fired or an explosive device is detonated, a pressure amplifier that amplifies pressure signals generated by the differential air pressure sensor, a microphone, a microphone amplifier that amplifies audio signals generated by the microphone, and a pulse counter that calculates a total event length;
    (b) a digital processor that processes the amplified signals from the differential air pressure sensor and the microphone; and
    (c) a data radio that generates alerts based on input from the differential air pressure sensor and the microphone;
    wherein the system determines whether a gunshot event or an explosive event has occurred based on a pressure length sensitivity setting, a microphone length sensitivity setting, and a correlation sensitivity setting;
    wherein the system is configured to differentiate between a gunshot and a non-gunshot explosive event by measuring the duration of the pressure event and the duration of the microphone event;
    wherein if the pressure event is longer than 240 mS and the microphone event is longer than 400 mS, the system determines that a non-gunshot explosive event has occurred;
    wherein the system is configured to differentiate between a single gunshot and multiple gunshots by generating an initial gunshot report, incrementing a gunshot counter, and starting a multiple gunshot window timer to determine whether more than one gunshot occurs during a preset period of time; and
    wherein the system is configured to generate a first type of alert in the event of a single gunshot and a second type of alert in the event of multiple gunshots.

2. The system of claim 1, wherein the amplified pressure signal is transmitted to a first hardware-based root mean square detector circuit that generates a first voltage output that is transmitted to a first hardware-based envelope detector that converts the first voltage output to a first digital square pulse that is transmitted to the digital processor; and
    wherein the amplified audio signal is transmitted to a second hardware-based root mean square detector circuit that generates a second voltage output that is transmitted to a second hardware-based envelope detector that converts the second voltage output to a second digital square pulse that is transmitted to the digital processor.

3. The system of claim 1, wherein when the device is powered, it undergoes a calibration process wherein the device reads a first sequence of analog microphone readings, average the readings, and notes a default baseline microphone audio level reference;

wherein an internal tone generator within the device generates a tone and reads a second sequence of microphone readings and averages the readings to determine a reference level change with and without a tone present; and wherein if the microphone calibration process is successful, an initialization message is sent to an alerting server, and all system variables are reset.

4. The system of claim 1, wherein an interrupt request process is initiated by a manual button push, a pressure-detected event, or a microphone-detected event;

wherein the system identifies a first-to-occur event by determining whether the manual button push event, the pressure-detected event or the microphone-detected event occurred first and sets a flag based on the first-to-occur event; and wherein the system determines whether the manual button push event, the pressure-detected event and the microphone-detected event are inactive, and if so, calls event processing.

5. The system of claim 4, wherein the pressure-detected event has a length, the microphone-detected event has a length, and the system determines whether the length of the pressure-detected event exceeds a first predetermined value and whether the length of the microphone-detected event exceeds a second predetermined value; and wherein the system identifies either the pressure-detected event or the microphone-detected event as a last-to-deactivate event, and wherein the system determines the total event length based on activation of the first-to-occur event and deactivation of the last-to-deactivate event.

6. The system of claim 5, wherein if the pressure-detected event occurs before the microphone-detected event, the system determines whether the microphone-detected event occurred within a predetermined period of time after the pressure-detected event occurred; and wherein the system determines whether the length of the microphone-detected event is longer than the length of the pressure-detected event; and wherein the system determines whether a gunshot or an explosion occurred based on the length of the microphone-detected event and the length of the pressure-detected event.

7. The system of claim 5, wherein if the microphone-detected event occurs before the pressure-detected event, the system determines whether the pressure-detected event occurred within a predetermined period of time after the microphone-detected event occurred;

wherein the system determines whether the length of the microphone-detected event is longer than the length of the pressure-detected event; and wherein the system determines whether a gunshot or an explosion occurred based on the length of the microphone-detected event and the length of the pressure-detected event.

8. The system of claim 1, wherein the differential air pressure sensor is a subsonic sensor.

9. The system of claim 1, wherein the hardware device further comprises an absolute air pressure sensor.

10. The system of claim 1, wherein the hardware device further comprises an accelerometer sensor.

11. The system of claim 1, wherein the hardware device further comprises a location receiver.

12. The system of claim 1, wherein the hardware device further comprises a manual alert button.

13. The system of claim 1, further comprising a gunshot counter that determines the number of gunshots detected within a window timer period.

* * * * *